United States Patent

Ju et al.

[11] Patent Number: 5,914,607
[45] Date of Patent: Jun. 22, 1999

[54] APPARATUS AND METHODS FOR ANALYZING A SAMPLE SOLUTION, INCLUDING FIRST AND SECOND ION DETECTORS

[75] Inventors: Jin-Ho Ju, Seoul; Sang-Kyong Kim; Sung-Chul Kang, both of Kyungki-do, all of Rep. of Korea

[73] Assignee: Samsung Electronics Co., Ltd., Rep. of Korea

[21] Appl. No.: 08/839,402

[22] Filed: Apr. 11, 1997

[30] Foreign Application Priority Data

Apr. 12, 1996 [KR] Rep. of Korea ...................... 96-10977

[51] Int. Cl.[6] .................................................. G01R 27/26
[52] U.S. Cl. .................... 324/439; 324/464; 205/789.5
[58] Field of Search .................................. 324/464, 459, 324/439; 205/789, 789.3; 204/400

[56] References Cited

U.S. PATENT DOCUMENTS 4,357,143  11/1982  Scott .................................... 205/789.5
4,440,602  4/1984  Dobson ............................... 205/789.5

FOREIGN PATENT DOCUMENTS

361025049  2/1986  Japan .................................. 205/789.5
403115849  5/1991  Japan .................................. 324/459
3252541  11/1991  Japan .................................. 324/459

*Primary Examiner*—Maura K. Regan
*Attorney, Agent, or Firm*—Myers Bigel Sibley & Sajovec

[57] ABSTRACT

A sample solution contained in a sample vessel is analyzed using a positive ion detector and a negative ion detector. The positive ion detector and the negative ion detector are supplied with the sample solution from the sample vessel, while isolating the positive ion detector and the negative ion detector from one another. Accordingly, the sample solution is not supplied from the positive ion detector to the negative ion detector, and the sample solution is not supplied from the negative ion detector to the positive ion detector. The positive ion detector and negative ion detector are preferably supplied with sample solution from the sample vessel using a bidirectional valve having an input port and first and second output ports. The input port is connected to the sample vessel, the first output port is connected to the first detector, and the second output port is connected to the second detector.

6 Claims, 7 Drawing Sheets

APPARATUS AND METHODS FOR ANALYZING A SAMPLE SOLUTION, INCLUDING FIRST AND SECOND ION DETECTORS

FIELD OF THE INVENTION

This invention relates to measuring and testing apparatus and methods, and more particularly to apparatus and methods for analyzing ions in a sample solution.

BACKGROUND OF THE INVENTION

Apparatus and methods for analyzing a sample solution are widely used in manufacturing operations. For example, in the manufacture of semiconductor devices, semiconductor wafers are often cleaned using deionized water. It is important to analyze the deionized water to insure that an acceptably low level of ions, including positive ions and negative ions, is present in the deionized water.

Figure 1:
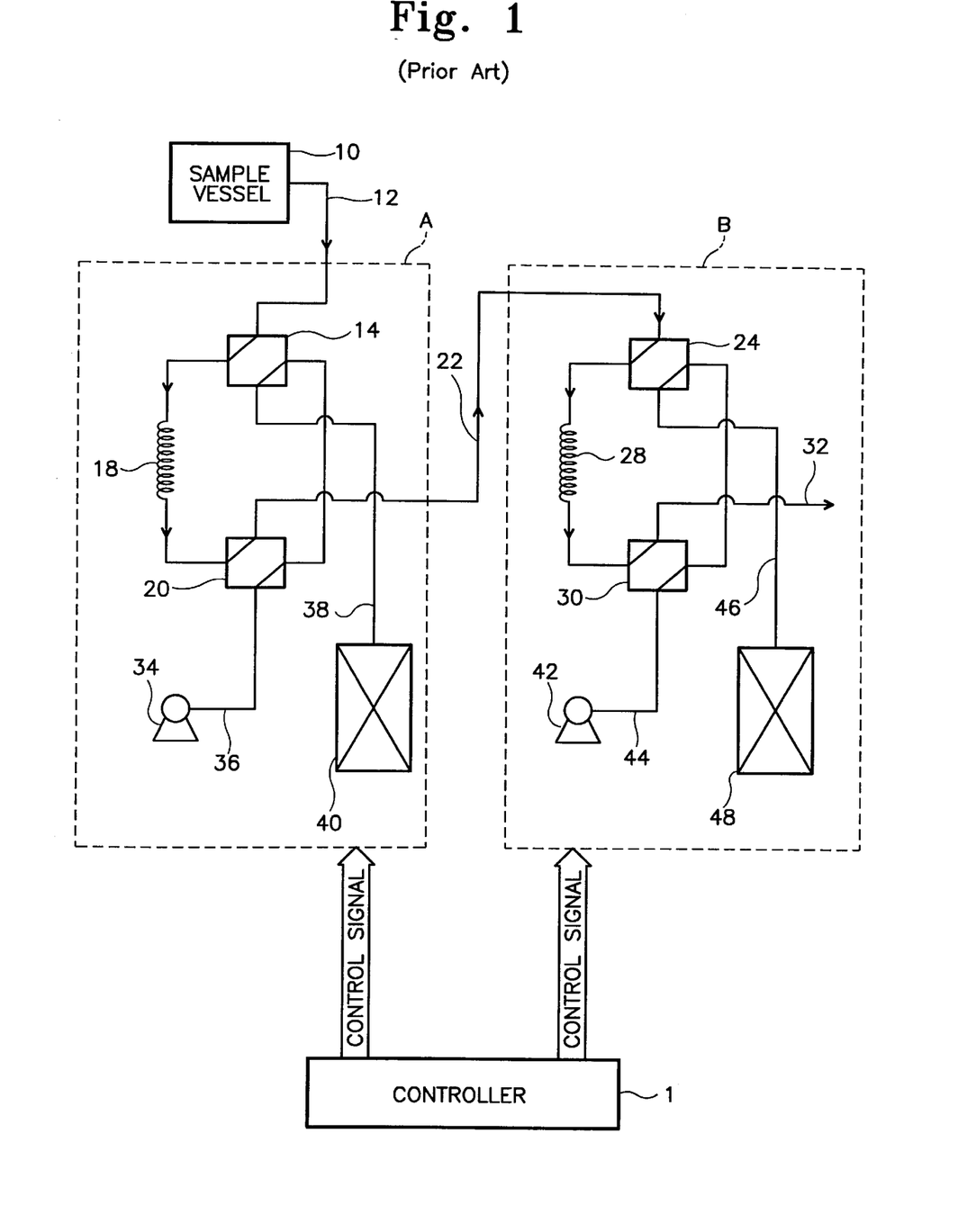

FIG. 1 shows a conventional solution analyzing apparatus illustrating a first solution flow channel. As illustrated by the arrows, a sample solution such as a sample semiconductor cleaning solution, contained in a sample vessel 10 is filled through a sample solution supply line 12 into a sample loop line 18 of a positive ion detector "A". The sample solution then continues to be filled through the sample loop line 18 into a sample loop line 28 of a negative ion detector "B".

The positive and negative ion detectors "A" and "B" are serially connected through a solution passing line 22. This line 22 is provided to transfer the sample solution through the sample loop line 18 of the positive ion detector "A" to the other sample loop line 28 of the negative ion detector "B". The sample vessel 10 generally contains a small amount of sample solution, for example, a cleaning solution of semiconductor substrates which is obtained from a main cleaning solution container (not shown).

Referring again to FIG. 1, the sample solution flows through the supply line 12 to the directional valve 14 of the positive ion detector "A". This valve 14 is controlled by a control signal from a controller 1 so that the sample solution can fill up the sample loop line 18. The filled sample solution of the sample loop line 18 passes through a directional valve 20 to the solution passing line 22 under control of the controller 1. The sample solution in the solution passing line 22 flows through a directional valve 24, the sample loop line 28 and a directional valve 30 of the negative ion detector "B" to an outlet line 32. This solution flow channel is formed by the directional valves which are controlled in response to the control signals of the controller to allow the sample solution to be filled into the sample loop lines 18 and 28 of the detectors "A" and "B". This solution flow step is hereinafter called a sample supplying step.

Figure 2:
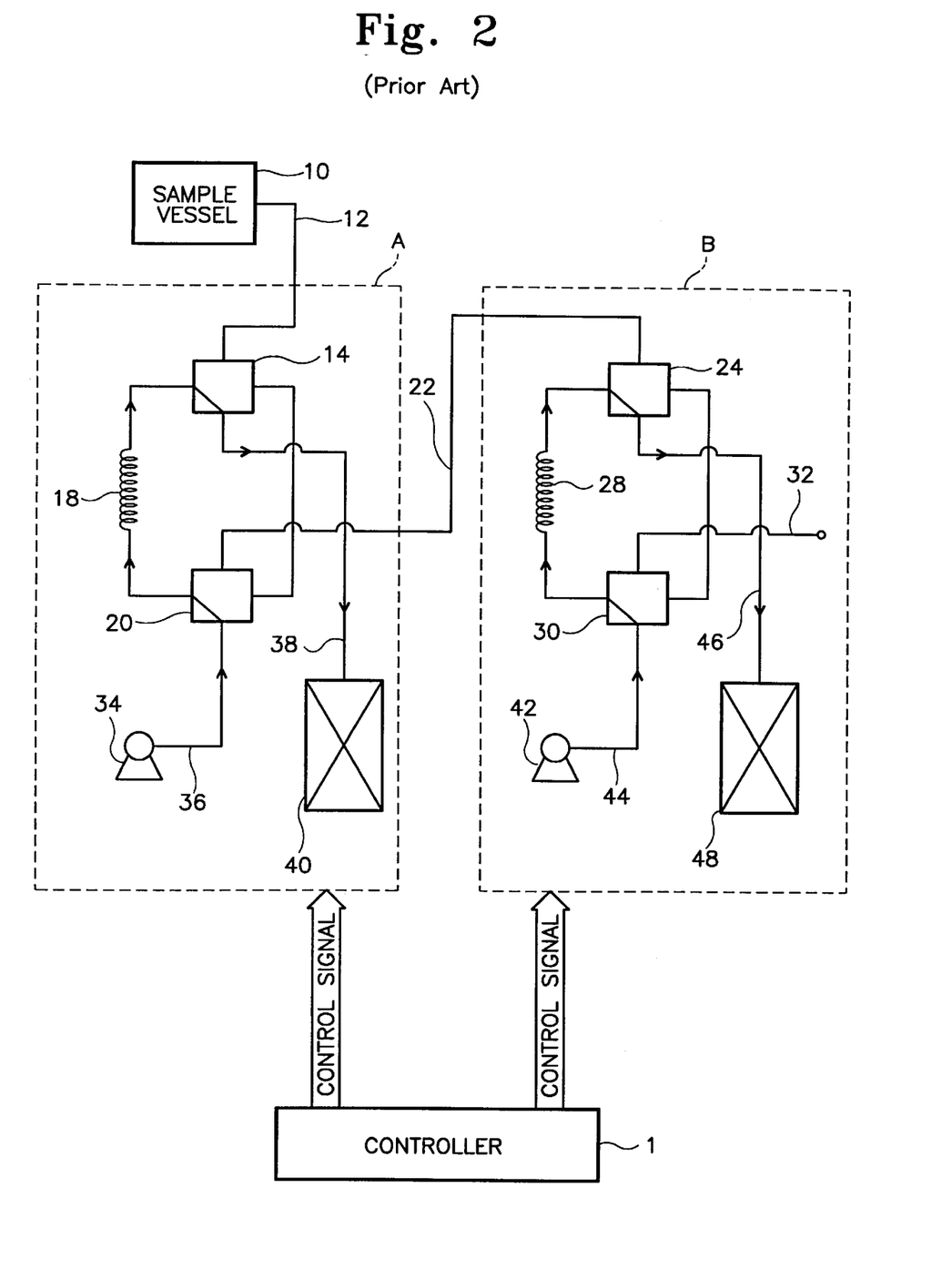

FIG. 2 shows the conventional solution analyzing apparatus illustrating a second solution flow channel in which the filled sample solution is supplied from the sample loop lines 18 and 28 to two conductivity detectors 40 and 48 respectively, one of which is provided to detect a positive ion component contained in the sample solution and the other of which detects a negative ion component contained in the sample solution. This solution flow channel is also formed by means of the directional valves in response to the control signals of the controller 1.

Referring again to FIG. 2, the filled sample solutions in the sample loop lines 18 and 28 flow through the directional valves 14 and 24 to the conductivity detectors 40 and 48, respectively. When pump 34 starts to operate in response to a control signal from the controller 1, a loading solution pumped by the pump 34 can flow through a loading solution supply line 36 to the directional valve 20. Then the sample solution filled in the sample loop line 18 is pushed up out of the sample loop line 18 and is provided to the conductivity detector 40. This solution flow step is hereinafter called a sample loading step. Because the directional valves are controlled in response to the control signals to form the solution supplying channel to the conductivity detector, the sample solution in the sample loop line 18 is supplied through the directional valve 14 to the conductivity detector 40. The conductivity detector 40 analyzes the supplied solution and detects a positive ion component.

Also, when pump 42 starts to operate in response to a control signal from the controller 1, a loading solution, for example, an HCl solution, pumped by the pump 42, can flow through a loading solution supply line 44 to the directional valve 30. The sample solution filled in the sample loop line 28 is pushed up out of the sample loop line 28 and is provided to the conductivity detector 48. Because the directional valves are controlled in response to the control signals to form the solution supplying channel to the conductivity detector, the sample solution in the sample loop line 28 is supplied through the directional valve 24 to the conductivity detector 48. The conductivity detector 48 analyzes the supplied solution and detects a negative ion component.

After detecting the ion components of the sample solution, if the conventional sample solution analyzing apparatus again detects a new sample solution, it is again operated according to the above described method. That is, a new sample solution from the sample vessel 10 is filled into the sample loop lines 18 and 28 through the first solution flow channel, as shown in FIG. 1, and then the filled solutions of the lines 18 and 28 are supplied to the conductivity detectors 40 and 48 through the second solution flow channel, as shown in FIG. 2. However, even though the new sample solution from the vessel 10 flows through the first solution flow channel so as to fill up the first and second sample loop lines 18 and 28 and the previously filled solution (i.e., HCl solution) in the sample loop lines 18 and 28 is dispensed through the outlet line 32, an extremely small amount of the HCl solution may remain in the sample loop line 28 of the negative ion detector "B". Because of the extremely small HCl solution which remains, it may be difficult for the conventional solution analyzing apparatus to accurately detect the ion components of the new sample solution, as shown in FIGS. 3 and 4.

Figure 3:
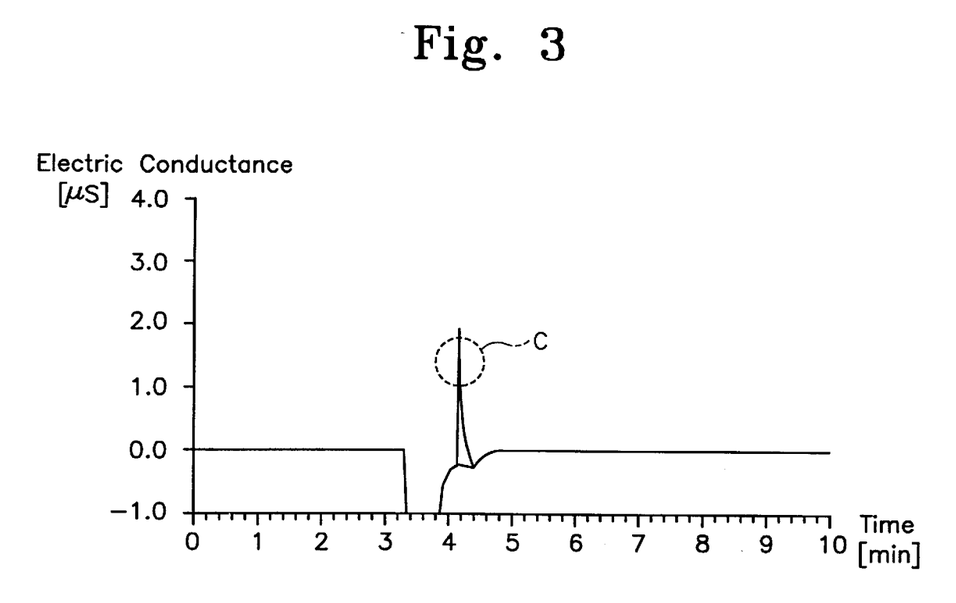
FIG. 3 is a graph showing an analysis result of negative ion components contained in the sample solution by using the conventional solution analyzing apparatus, when deionized water is used as the sample solution and an HCl solution is used as a loading solution.

From FIG. 3, it can be seen that, when deionized water is used as a sample solution, a peak value "C" is detected at about 4.2 minutes during the detection of negative ion components contained in the deionized water. Here, the peak value indicates that the deionized water is contaminated with the loading solution, for example, an extremely small HCl solution, remaining in the sample loop line 28.

Figure 4:
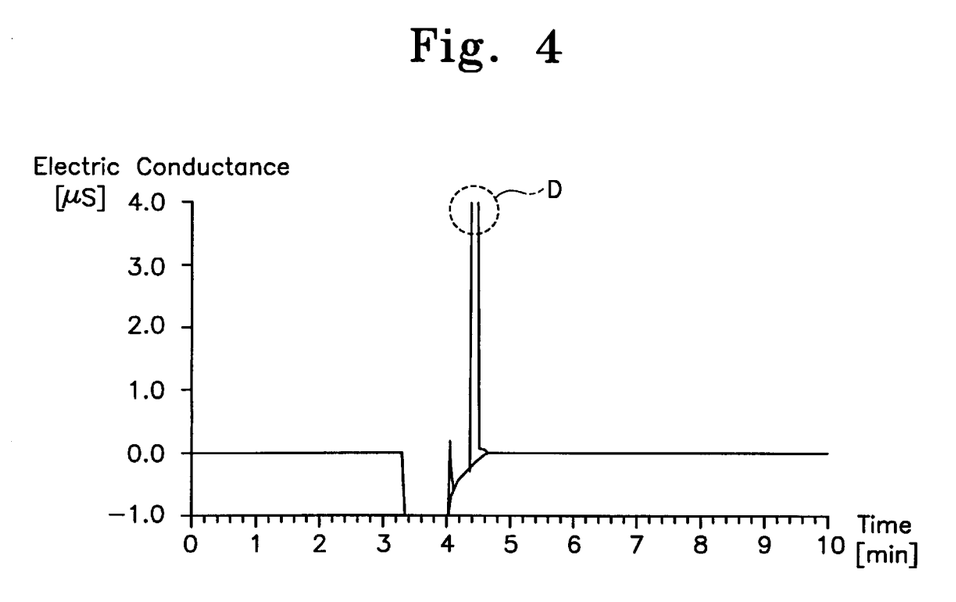
FIG. 4 is a graph showing an analysis result of positive ion components contained in the sample solution by using the conventional solution analyzing apparatus, when deionized water is used as the sample solution and an MSA (methane sulfonic acid) solution is used as a loading solution.

In addition, when analyzing a component indicating the peak value by high performance ion chromatography, and an MSA (methane sulfonic acid) solution is used as a loading solution and deionized water is used as a sample solution, a large peak value "D" may be found as shown in FIG. 4. This is because the sample loop line 28 of the negative ion detector "B" has been contaminated with the MSA solution.

Accordingly, since negative ion components $Cl^-$ of the HCl solution or positive ion components of MSA may contaminate the sample loop line 28 during the sample loading step, it may be difficult to accurately detect an extremely small ion component contained in the sample solution. Also, even if the sample solution supply line 12 is connected to the ion detector "B", it may be difficult to accurately detect an extremely small ion component contained in the sample solution. This is because ion components of the loading solution may contaminate the sample loop line 18 of the ion detector "A".

SUMMARY OF THE INVENTION

It is therefore an object of the present invention to provide improved apparatus and methods for analyzing a sample solution to detect ion components therein.

It is yet another object of the present invention to provide apparatus and methods for analyzing a sample solution which can reduce contamination in the ion detectors thereof.

These and other objects are provided according to the present invention by apparatus for analyzing a sample solution including a sample vessel which contains the sample solution, a positive ion detector, a negative ion detector and means for supplying the positive ion detector and the negative ion detector with the sample solution from the sample vessel, while isolating the positive ion detector and the negative ion detector from one another. As such, the sample solution is not supplied from the positive ion detector to the negative ion detector and the sample solution is not supplied from the negative ion detector to the positive ion detector. Reduced contamination may thereby be provided.

In particular, according to the present invention, an apparatus for analyzing a sample solution includes a sample vessel which contains the sample solution. The apparatus further comprises first detecting means which includes first storing means for storing the sample solution and first conductivity detecting means, responsive to the first storing means, for detecting first conductivity ion components in the sample solution. The apparatus also comprises second detecting means which includes second storing means for storing the sample solution and second conductivity detecting means, responsive to the second storing means, for detecting second conductivity ion components in the sample solution. The apparatus also includes means for selectively directing the sample solution from the sample vessel to the first detecting means and to the second detecting means.

In a preferred embodiment, the selectively directing means comprises a bidirectional valve having an input port and first and second output ports. The input port is connected to the sample vessel. The first output port is connected to the first detecting means, and the second output port is connected to the second detecting means.

In a preferred embodiment, the first detecting means also comprises first pumping means for pumping the sample solution from the first storing means into the first conductivity detecting means. The second detecting means further comprises second pumping means for pumping the sample solution from the second storing means into the second conductivity detecting means. A controller is also included for controlling the first detecting means, the second detecting means and the selectively directing means. Accordingly, the first and second detecting means are isolated from one another so that contamination is reduced or eliminated.

According to method aspects of the present invention, a sample solution contained in a sample vessel is analyzed using a positive ion detector and a negative ion detector. The sample solution is analyzed by supplying the positive ion detector and the negative ion detector with the sample solution from the sample vessel, while isolating the positive ion detector and the negative ion detector from one another. As such, the sample solution is not supplied from the positive ion detector to the negative ion detector and the sample solution is not supplied from the negative ion detector to the positive ion detector.

A preferred embodiment of methods according to the present invention, supplies the sample solution from the sample vessel to a first sample loop line and supplies the sample solution from the sample vessel to a second sample loop line. The sample solution is loaded from the first sample loop line to the positive ion detector and the sample solution is loaded from the second sample loop line to the negative ion detector. Positive ions are detected in the positive ion detector and negative ions are detected in the negative ion detector. It will be understood by those having skill in the art that the order of occurrence of the supplying, loading and detecting steps may be varied.

In a preferred embodiment, the step of loading the sample solution from the first sample loop line to the positive ion detector comprises the step of injecting a loading solution into the first sample loop line, to thereby load the sample solution from the first sample loop line to the positive ion detector. The step of loading the sample solution from the second sample loop line to the negative ion detector comprises the step of injecting a loading solution into the second sample loop line, to thereby load the sample solution from the second sample loop line to the negative ion detector. After the positive ions are detected, the sample solution is flushed from the first sample loop line. After the negative ions are detected in the negative ion detector, the second sample loop line is also flushed.

Accordingly, contamination of a sample loop line by a loading solution may be reduced or eliminated.

BRIEF DESCRIPTION OF THE DRAWINGS

FIGS. 1 and 2 are schematic diagrams of a conventional solution analyzing apparatus, wherein FIG. 1 shows a first solution flow channel to fill a sample solution from a sample vessel into two sample loop lines of ion component detectors, and FIG. 2 shows a second solution flow channel to supply the filled sample solution to two conductivity detectors;

FIGS. 5 and 6 are schematic diagrams of solution analyzing apparatus and methods of the present invention, wherein FIG. 5 shows a solution flow channel in which a sample solution from a sample vessel is filled in a first sample loop line of a positive ion detector, and FIG. 6 shows another solution flow channel in which a sample solution from the sample vessel is filled in a second sample loop line of a negative ion detector;

DETAILED DESCRIPTION OF PREFERRED EMBODIMENTS

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 5:
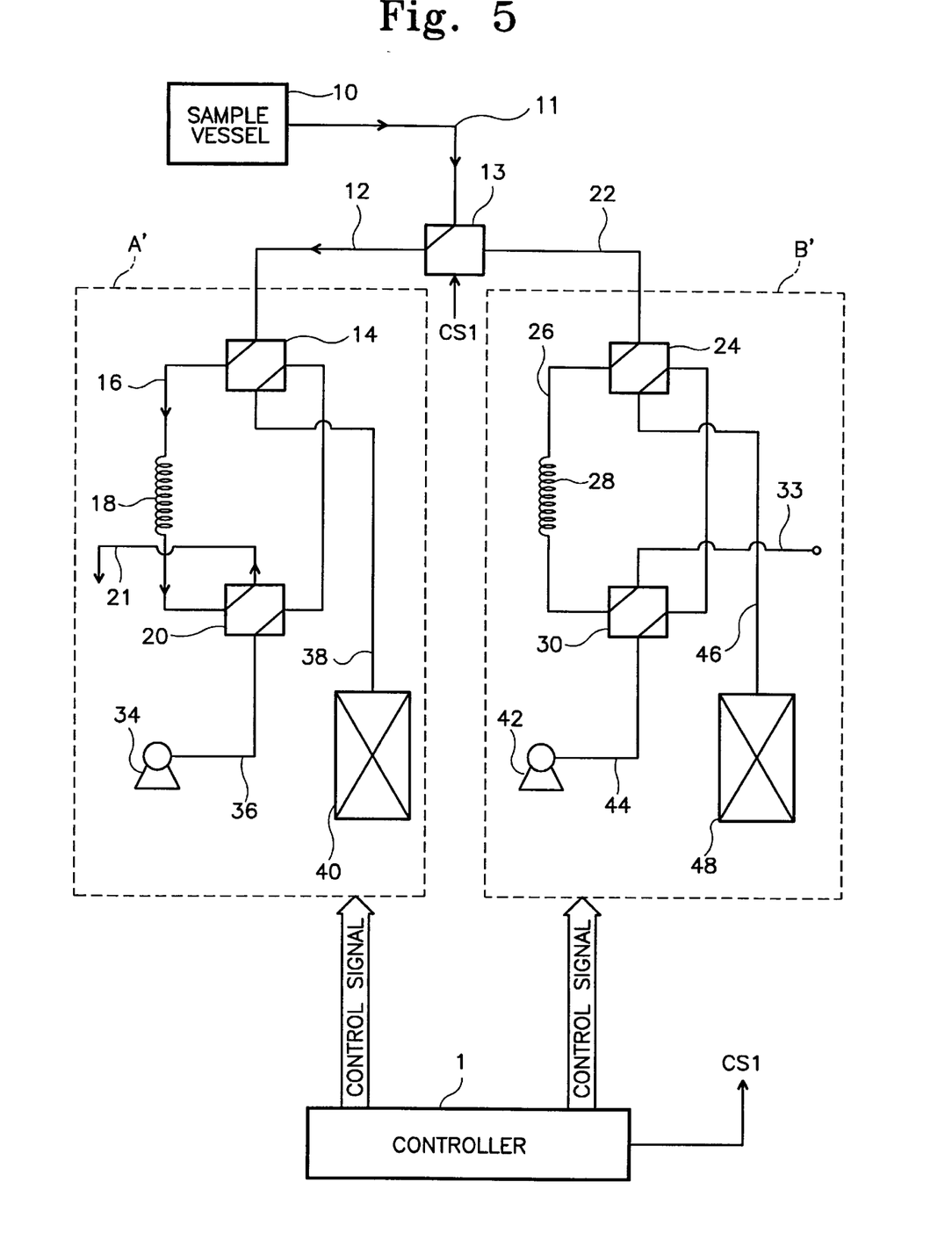
Figure 6:
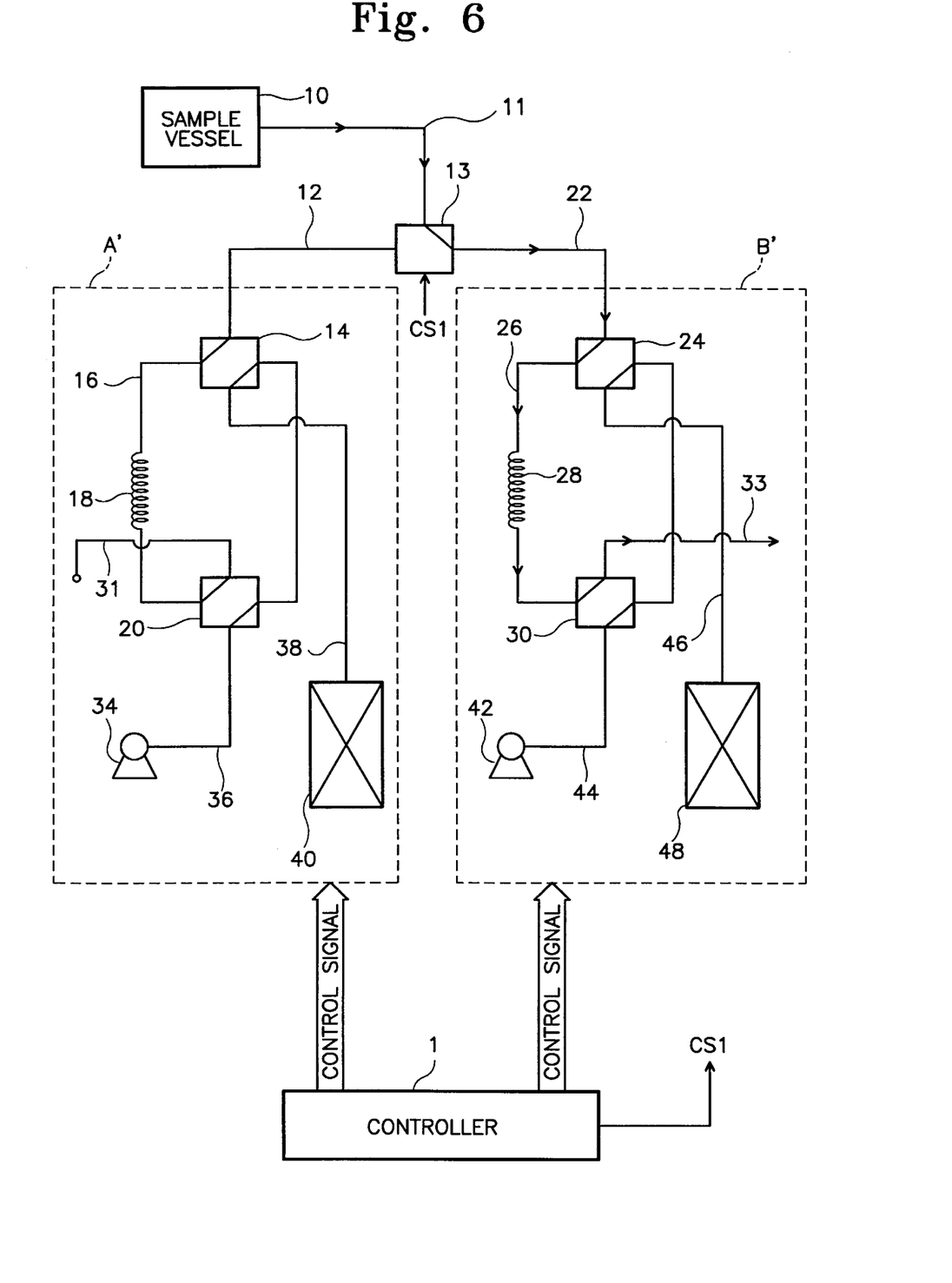
Figure 7:
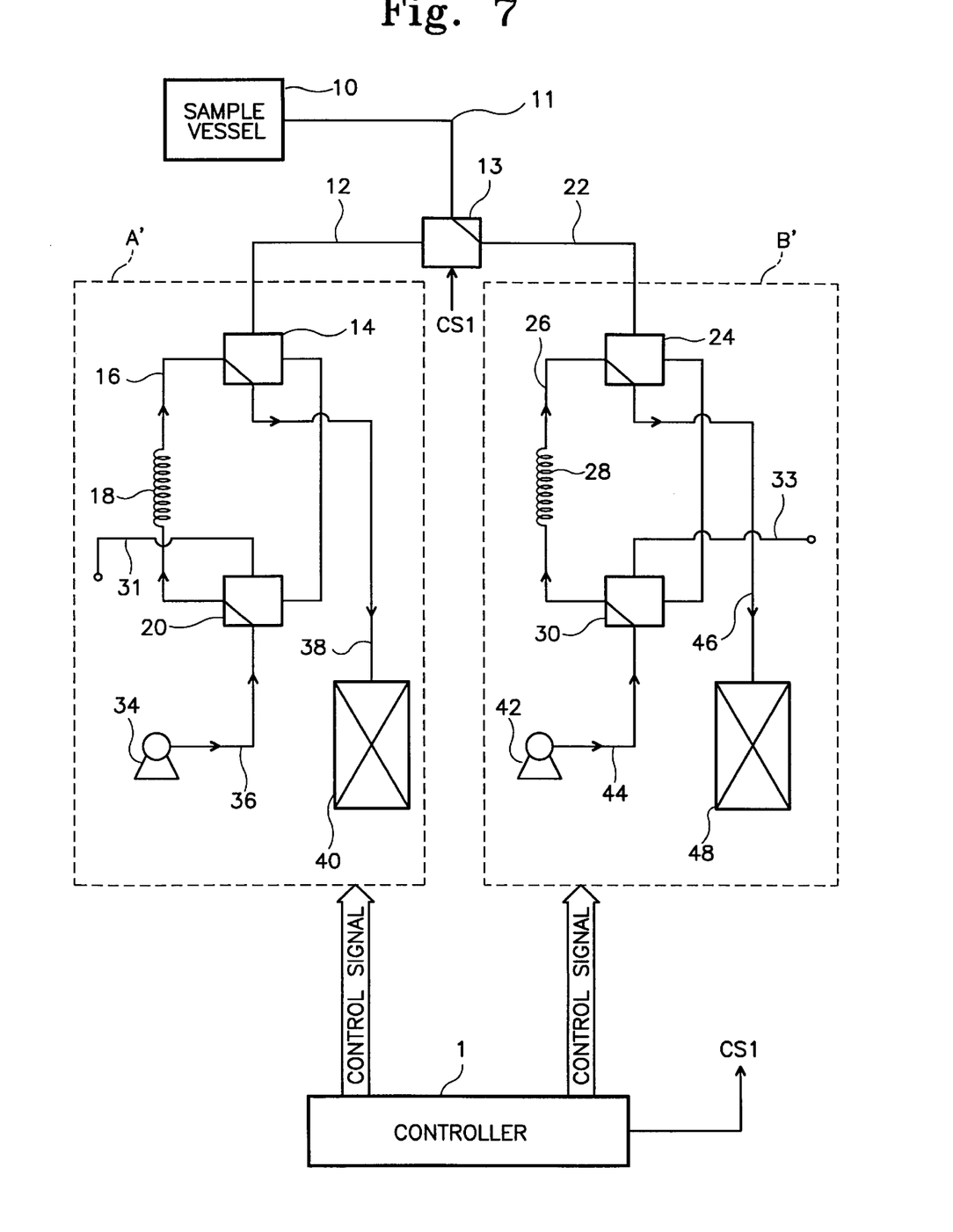
FIG. 7 is a schematic diagram of solution analyzing apparatus and methods of the present invention when the sample solutions filled in the first and second sample loop lines are supplied to conductivity detectors respectively.

Referring to FIGS. 5 through 7, solution analyzing apparatus and methods in accordance with the present invention comprise a channel selecting valve 13 which is connected between a sample vessel 10 and a positive ion detector "A'" or a negative ion detector "B'", and which selectively supplies a sample solution from the vessel 10 to the positive or the negative ion detector "A'" or "B'" in response to a control signal CS1 from a controller 1. It will be understood by those having skill in the art that means for selectively directing the sample solution from the sample vessel to the positive and negative ion detectors, other than a bidirectional valve, may be provided. With this construction, the sample solution from the sample vessel 10 is supplied directly to a first or a second sample loop line 18 or 28 of the positive or the negative ion detector by the channel selecting valve 13, in what is hereinafter called a sample supplying step. The sample solutions filled in the sample loop lines 18 and 28 are loaded to the conductivity detectors 40 and 48 by means of the controller 1, in what is called a sample loading step.

During the sample loading step, the filled sample solutions of the sample loop lines 18 and 28 are pushed up from the sample loop lines to the conductivity detectors 40 and 48 by loading solutions pumped by pumps 34 and 42, respectively. The loading solution is provided to load the filled solution of the lines 18 and 28 into the conductivity detectors. After the sample loading step, when a new sample solution is again filled from the vessel 10 into the sample loop line 18 or 28, a previously loaded loading solution therein can be completely dispensed from the sample loop line 18 or 28. This is because the new sample solution is not supplied through the positive ion detector "A'" to the negative ion detector "B'", but is supplied directly to the positive or the negative ion detector by means of the channel selecting valve 13.

A cleaning solution for semiconductor substrates may be used as the sample solution. This cleaning solution generally comprises deionized water. Also the loading solution can be selected depending on the kinds of sample solutions. If deionized water is used as a sample solution, an HCl solution may be used as a loading solution. The channel selecting valve 13 comprises a bidirectional valve having an input port and first and second output ports. The input port is connected to the sample vessel 10. The first output port is connected to the positive ion detector "A'" and the second output port is connected to the negative ion detector "B'".

The sample supplying steps of solution analyzing apparatus and methods according to the invention will now be described in detail with reference to FIGS. 5 and 6. In FIG. 5, it is illustrated that a sample solution from a sample vessel is filled in first sample loop line 18 of the positive ion detector "A'". The sample solution from the sample vessel 10 is supplied via a main supply line 11 to the channel selecting valve 13. This valve 13 permits the sample solution to be provided to positive ion detector "A'" in response to a control signal CS1 from controller 1. A solution flow channel to the positive ion detector "A'" is then opened by the channel selecting valve 13, and another solution flow channel to the negative ion detector "B'" is closed. The sample solution introduced to the positive ion detector "A'" is supplied via a sub supply line 12 to a directional valve 14 of the detector "A'". This valve 14 is also controlled by another control signal from the controller 1 to permit the sample solution to flow via a sample loop line 18 and a directional valve 20 to an outlet line 21. Thus, the sample loop line 18 is filled with the sample solution.

As described immediately above, when the sample solution is filled in the sample loop line 18 of the positive ion detector "A'", the channel selecting valve 13 is again controlled in response to the control signal CS1 from the controller 1 so that a sample solution from the sample vessel 10 is filled in a second sample loop line 28 of the negative ion detector "B'", as shown in FIG. 6. As shown, the channel selecting valve 13 permits the sample solution to be provided to the negative ion detector "B'" in response to the control signal CS1 from the controller 1. The solution flow channel to the positive ion detector "B'" is then opened by the channel selecting valve 13 and the solution flow channel to the positive ion detector "A'" is closed. The sample solution introduced to the negative ion detector "B'" is supplied via a sub supply line 22 to a directional valve 24 of the detector "B'". This valve 24 is also controlled by another control signal from the controller 1 to permit the sample solution to flow via the sample loop line 28 and a directional valve 30 to an outlet line 33. Thus, the sample loop line 28 is filled with the sample solution.

With reference to FIG. 7, according to solution analyzing apparatus and methods of the present invention, the sample solutions filled in the first and second sample loop lines 18 and 28 are supplied to conductivity detectors 40 and 48, respectively, one of which is provided to detect a positive ion component contained in the sample solution filled in the sample loop line 18 and the other to detect a negative ion component contained in the sample solution filled in the sample loop line 28.

The sample loading step will now be described in detail with reference to FIG. 7. The sample loading step indicates that the sample solution filled in the first sample loop line 18 flows through the directional valve 14 to the conductivity detector 40. Referring to FIG. 7, if pump 34 starts to operate in response to another control signal from the controller 1, a loading solution, for example, an HCl solution pumped by the pump 34, can flow through a loading solution supply line 36 to the directional valve 20. The sample solution filled in the sample loop line 18 is then pushed up out of the sample loop line 18 and provided to the conductivity detector 40. Also, because the directional valves 14 and 20 are controlled in response to the control signals to form the sample loading channel to the conductivity detector 40, the sample solution in the sample loop line 18 is loaded through the directional valve 14 to the conductivity detector 40. Here, the conductivity detector 40 analyzes the loaded solution and detects positive ion components thereof.

Similarly, when a pump 42 starts to operate in response to a control signal from the controller 1, a loading solution pumped by the pump 42 can flow through a loading solution supply line 44 to the directional valve 30. Then the sample solution filled in the sample loop line 28 is pushed up out of the sample loop line 28 and provided to the conductivity detector 48. Because the directional valves 24 and 30 are controlled in response to the control signals to form the sample loading channel to the conductivity detector 48, the sample solution in the sample loop line 28 is loaded through the directional valve 24 to the conductivity detector 48. The conductivity detector 48 analyzes the loaded solution and detects negative ion components.

Figure 8:
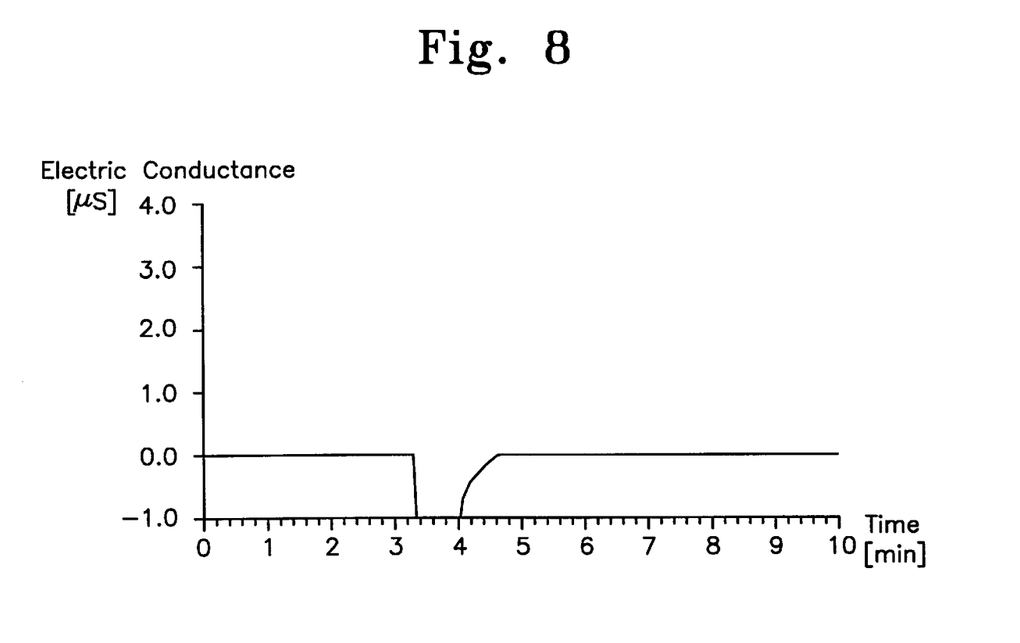
FIG. 8 is a graph showing an analysis result of negative ion components contained in the sample solution by using solution analyzing apparatus and methods of the present invention, when deionized water is used as the sample solution and an HCl solution is used as a loading solution.

As described above, even when solution analyzing apparatus and methods of the present invention receive a new sample solution and detect ion components of the new sample after detecting the ion components of the previously loaded sample solution, they can accurately detect the ion components of the new sample solution, as shown in FIG. 8. This is because loading solutions previously filled in the first and the second sample loop lines 18 and 28 during the sample loading step may be dispensed directly to the outlet lines 31 and 33, respectively. Thus, an extremely small amount thereof does not remain in the sample loop lines when the new sample solution is filled in the sample loop lines.

FIG. 8 shows an analysis result of negative ion components contained in the sample solution using solution analyzing apparatus and methods of the invention, when deionized water is used as the sample solution and an HCl solution as a loading solution. It can be seen from the FIG. 8 that no peak value is detected during the detection of negative ion components contained in the deionized water.

Thus, according to solution analyzing apparatus and methods of the present invention, sample loop lines are not contaminated with a loading solution and therefore ion components of a sample solution can be accurately detected.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed:

1. An apparatus for analyzing a sample solution, comprising:

a sample vessel which contains said sample solution;

a positive ion detector;

a negative ion detector; and means for supplying said positive ion detector and said negative ion detector with said sample solution from said sample vessel, while isolating said positive ion detector and said negative ion detector from one another, such that said sample solution is not supplied from said positive ion detector to said negative ion detector and said sample solution is not supplied from said negative ion detector to said positive ion detector.

2. An apparatus according to claim 1 wherein said supplying means comprises a bidirectional valve which supplies said positive ion detector and said negative ion detector with said sample solution from said sample vessel.

3. A method for analyzing a sample solution contained in a sample vessel, using a positive ion detector and a negative ion detector, said method comprising the step of:

supplying said positive ion detector and said negative ion detector with said sample solution from said sample vessel, while isolating said positive ion detector and said negative ion detector from one another, such that said sample solution is not supplied from said positive ion detector to said negative ion detector and said sample solution is not supplied from said negative ion detector to said positive ion detector.

4. A method according to claim 3 which also uses a first sample loop line connected to said positive ion detector and a second sample loop line connected to said negative ion detector, said supplying step comprising the steps of:

supplying said sample solution from said sample vessel to said first sample loop line;

supplying said sample solution from said sample vessel to said second sample loop line;

loading said sample solution from said first sample loop line to said positive ion detector;

loading said sample solution from said second sample loop line to said negative ion detector;

detecting positive ions in said positive ion detector; and detecting negative ions in said negative ion detector.

5. A method according to claim 4:

wherein said step of loading said sample solution from said first sample loop line to said positive ion detector comprises the step of injecting a loading solution into said first sample loop line to thereby load said sample solution from said first sample loop line to said positive ion detector; and wherein said step of loading said sample solution from said second sample loop line to said negative ion detector comprises the step of injecting a loading solution into said second sample loop line to thereby load said sample solution from said second sample loop line to said negative ion detector.

6. A method according to claim 4:

wherein said step of detecting positive ions in said positive ion detector is followed by the step of flushing said first sample loop line; and wherein said step of detecting negative ions in said negative ion detector is followed by the step of flushing said second sample loop line.

* * * * *